United States Patent [19]

Drabb et al.

[11] Patent Number: 5,973,154
[45] Date of Patent: Oct. 26, 1999

[54] PROCESS FOR THE PREPARATION OF CHIRAL IMIDAZOLINONE HERBICIDES

[75] Inventors: Thomas Walter Drabb, Trenton; Peter John Wepplo, Princeton, both of N.J.

[73] Assignee: American Cyanamid Company, Madison, N.J.

[21] Appl. No.: 09/303,967

[22] Filed: May 3, 1999

[51] Int. Cl.$^6$ .................................................. C07D 401/04
[52] U.S. Cl. ........................................ 546/167; 546/274.1
[58] Field of Search .................................. 546/167, 274.1

[56] References Cited

U.S. PATENT DOCUMENTS 4,683,324   7/1987   Gastrock et al. .
4,758,667   7/1988   Szczepanski et al. .

*Primary Examiner*—Patricia L. Morris
*Attorney, Agent, or Firm*—John W. Hogan, Jr.

[57] ABSTRACT

There is provided a process for the preparation of essentially enantiomerically pure imidazolinone herbicides having the R-configuration via (R)2-amino-2,3-dimethylbutyramide.

10 Claims, No Drawings

PROCESS FOR THE PREPARATION OF CHIRAL IMIDAZOLINONE HERBICIDES

BACKGROUND OF THE INVENTION

Imidazolinone compounds, for instance, those described in U.S. Pat. No. 4,798,619 and U.S. Pat. No. 5,334,576, are highly potent, broad spectrum, environmentally benign, herbicidal agents. In general, the herbicidal activity of the R-isomer is approximately twice that of the racemic imidazolinone compound. A process to prepare chiral imidazolinones via the resolved optically active 2-amino-2,3-dimethylbutyramide enantiomers and a process to prepare said aminoamide enantiomers are described in U.S. Pat. No. 4,683,324. However, the chiral imdazolinone compounds prepared therein require 3 separate process steps. Szczepanski and Dürr describe a 2 step process to prepare racemic imdazolinone herbicides via the reaction of a racemic 2-aminoalkane carboxamide and a suitably substituted pyridine-2,3-dicarboxylate in U.S. Pat. No. 4,758,667. However, no reference or guidance to chiral imidazolinone preparation is described therein.

Accordingly, it is an object of this invention to provide a process to prepare essentially enantiomerically pure imidazolinone herbicidal agents directly from (R)2-amino-2,3-dimethylbutyramide in a simple manner and good yield and with substantially complete retention of optical purity.

SUMMARY OF THE INVENTION

The present invention provides a stereospecific process to prepare a chiral compound of formula I

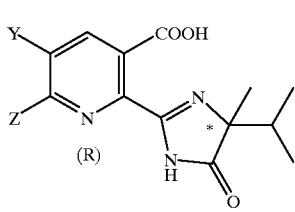

wherein
Y and Z are each independently H, $C_1$–$C_4$alkyl optionally substituted with one $C_1$–$C_4$alkoxy group or Y and Z may be taken together to form a group —CH=CH—CH=CH—
which process comprises: reacting a compound of formula II

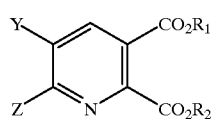

wherein Y and Z are as described hereinabove and $R_1$ and $R_2$ are each independently $C_1$–$C_8$alkyl, phenyl or phenyl ($C_1$–$C_4$)alkyl (preferably methyl or ethyl) with at least one molar equivalent of (R)2-amino-2,3-dimethylbutyramide in the presence of a strong base and a non-polar, essentially water-free solvent to form a salt of the formula I compound; and treating said salt with aqueous acid to obtain the chiral free carboxylic acid of formula I.

DETAILED DESCRIPTION OF THE INVENTION

Chiral imidazolinone compounds having the R configuration demonstrate about a 2-fold increase in herbicidal activity over the corresponding racemic mixture. Heretofore, (R)imidazolinone compounds were prepared from (R)2-amino-2,3-dimethylbutyramide via the 3 step process described in U.S. Pat. No. 4,683,324. Advantageously, it has now been found that chiral imidazolinone herbicides may be prepared directly from (R)2-amino-2,3-dimethylbutyramide in a simple 2 step process with good yield and with substantially complete retention of enantiomeric purity from said (R)aminoamide starting material to the final chiral imidazolinone herbicidal product. Further, it has been found that the essential absence of water in the first process step leads to enhanced product yield and purity. The compounds of formula I are preferably those in which Y and Z are independently H, methyl, ethyl, methoxymethyl or form a group —CH=CH—CH=CH—. The following formula I compounds are especially preferred: (R)2-(4-isopropyl-4-methyl-5-oxo-2-imidazolin-2-yl) nicotinic acid; (R)2-(4-isopropyl-4-methyl-5-oxo-2-imidazolin-2-yl)-3-quinolincarboxylic acid; (R)2-(4-isopropyl-4-methyl-5-oxo-2-imidazolin-2-yl)-5-methylnicotinic acid; (R)5-ethyl-2-(4-isopropyl-4-methyl-5-oxo-2-imidazolin-2-yl)nicotinic acid; and (R)2-(4-isopropyl-4-methyl-5-oxo-2-imidazolin-2-yl)-5-(methoxymethyl)nicotinic acid.

In accordance with the process of the invention, a formula II diester is reacted with at least one molar equivalent of (R)2-amino-2,3-dimethylbutyramide in the presence of a strong base and a non-polar, essentially water-free solvent to form a salt of the formula I compound; said salt is treated with aqueous acid to form the desired chiral free acid of formula I. The process is illustrated in flow diagram I. In the specification and claims, an asterisk designates the assymetric carbon upon which the (R) configuration is conferred.

Flow Diagram I

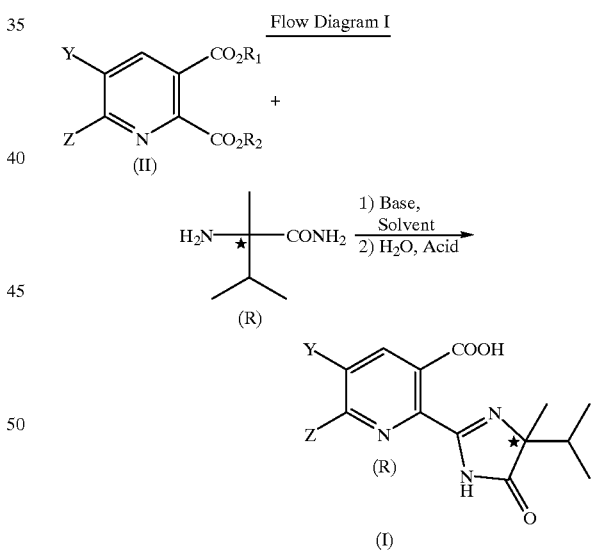

Bases suitable for use in the method of the invention are strong bases such as alkali metal hydroxides and alkali metal alkoxides, preferably alkali metal alkoxides, more preferably alkali metal $C_1$–$C_4$alkyl alkoxides such as sodium t-butoxide, potassium t-butoxide, sodium methoxide, potassium methoxide, sodium ethoxide, potassium ethoxide, and the like. The base may be present in at least one mole per mole of the formula II diester, preferably 1.5 mole to 2.5 mole of base per mole of diester. Although greater amounts of base may be used, excess base may lead to decreased product yield and/or purity.

Solvents suitable for use in the process of the invention are non-polar, essentially water-free solvents such as aromatic hydrocarbons (e.g. toluene, benzene, xylene, naphthalene and the like, preferably toluene), halogenated aromatic hydrocarbons (e.g. chlorobenzene, dichlorobenzenes and the like), hydrocarbons (e.g. pentanes, hexanes and the like), halogenated hydrocarbons (e.g. chloroform, methylene chloride, dichlorethane, and the like, esters (e.g. ethyl acetate, methyl propionate and the like), ethers (e.g. diethyl ether, tetrahydrofuran, dioxane and the like) or any of the conventional, preferably water immiscible, organic non-polar solvents.

Preferred non-polar, essentially water-free solvents suitable for use in the process of the invention are aromatic hydrocarbons, particularly toluene.

Acids suitable for use in the process of the invention include strong mineral acids such as HCl, HBr or $H_2SO_4$, preferably HCl or $H_2SO_4$.

In the inventive process, reaction temperature is directly related to reaction rate, e.g. the higher the reaction temperature, the faster the reaction rate. However, excessively high temperatures may lead to side-reactions and degradation products. In general, reaction temperatures of from room temperature to the reflux temperature of the solvent are suitable for use in the process of the invention. Preferred temperatures for use in the process of the invention are temperatures of about 50° C. to 90° C.

It is also intended that the process of the invention embrace the use of (S)2-amino-2,3-dimethylbutyramide to prepare the corresponding (S)-imidazolinone herbicidal product.

In actual practice, a mixture of the formula II diester and (R)2-amino-2,3-dimethylbutramide in a non-polar, essentially water-free solvent, preferably an aromatic hydrocarbon, more preferably toluene, is treated with at least one mole, preferably about 1.5 mole to 2.5 mole, of a strong base, preferably an alkali metal alkoxide, more preferably potassium t-butoxide, at a temperature of about room temperature to the boiling point of the solvent, preferably about 50° C. to 90° C., to form a salt of the chiral formula I compound. The thus-formed salt is acidified with aqueous acid, preferably aqueous HCl or $H_2SO_4$, to a pH of about 2 to 4 to obtain the desired chiral formula I imidazolinone herbicidal product as the free acid. The chiral product may be isolated using conventional procedures such as filtration, extraction with a suitable solvent, chromatographic separation and the like, preferably filtration or extraction.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight. NMR designates nuclear magnetic resonance.

EXAMPLE 1

Preparation of (R)2-(4-isopropyl-4-methyl-5-oxo-2-imidazolin-2-yl)-5-methylnicotinic acid

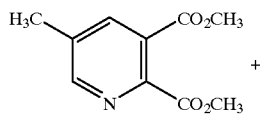

-continued

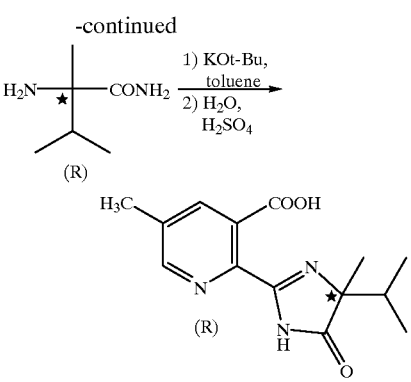

A stirred mixture of dimethyl 5-methylpyridine-2,3-dicarboxylate (52.25 g, 0.25 mol) and (R)2-amino-2,3-dimethylbutyramide (33.43 g, 0.2563 mol, 96.2% R isomer) in dry toluene is treated with KOt-Bu (29.4 g, 0.2625 mol) at 35° C., stirred at ambient temperatures for 10 minutes, treated with a second portion of KOt-Bu (29.4 g, 0.2625 mol) at 40° C., heated at 80°–85° C. for 1.5–2.0 hr, cooled to room temperature, treated with water and stirred until dissolution of solids is complete. The phases are separated. The aqueous phase is acidified to pH 3 with concentrated HCl, stirred at pH 3 for 10–15 min., and filtered. The aqueous filtrate is extracted with methylene chloride. The filtercake is dispersed in methylene chloride and the dispersion is filtered. The methylene chloride extracts and the methylene chloride filtrate are combined, dried over $MgSO_4$ and concentrated to dryness in vacuo to give the title product as a white solid, 47.3 g, 68.6% yield, 98.1% pure, 97% R isomer by quantitative NMR analysis.

EXAMPLE 2

Preparation of (R)2-(4-isopropyl-4-methyl-5-oxo-2-imidazolin-2-yl)-5-(methoxymethyl)nicotinic acid

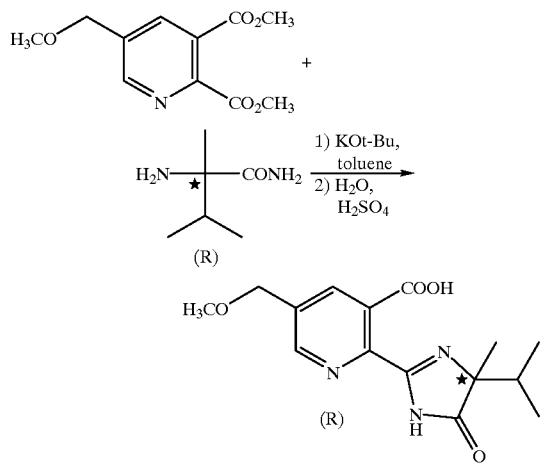

A mixture of dimethyl 5-(methoxymethyl)pyridine-2,3-dicarboxylate (215.4 g, 0.90 mol) and (R)2-amino-2,3-dimethylbutyramide (120.4 g, 0.923 mol, 96.2% R isomer) in dry toluene is stirred at room temperature for 15 minutes, treated with KOt-Bu (105.9 g, 0.945 mol), stirred at ambient temperatures for 5 minutes, treated with a second portion of KOt-Bu (105.9 g, 0.945 mol) at 30°–38° C., heated at 80° C.–85° C. for 1.5–2.0 hr, cooled to room temperature and diluted with water. The phases are separated. The aqueous phase is acidified to pH3 with concentrated HCl and extracted with methylene chloride. The extracts are combined, dried over $MgSO_4$, slurried in $SiO_2$ and filtered. The filtrate is concentrated in vacuo to dryness to give the title product as a cream-colored solid, 202.1 g (73.5% yield) 94.2% pure, 97% R isomer by quantitative NMR analysis.

What is claimed is:

1. A process for the preparation of a chiral compound of formula I

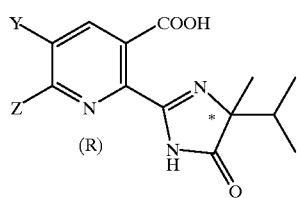

wherein

Y and z are each independently H, $C_1$–$C_4$alkyl optionally substituted with one $C_1$–$C_4$alkoxy group or Y and Z may be taken together to form a group —CH═CH—CH═CH— which process comprises: reacting a compound of formula II

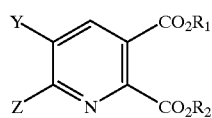

wherein Y and Z are as described hereinabove and $R_1$ and $R_2$ are each independently $C_1$–$C_8$alkyl, phenyl or phenyl ($C_1$–$C_4$)alkyl with at least one molar equivalent of (R)2-amino-2,3-dimethylbutyramide in the presence of a strong base and a non-polar, essentially water-free solvent to form a salt of the formula I compound; and treating said salt with aqueous acid to obtain the chiral free carboxylic acid of formula I.

2. The process according to claim 1 wherein the acid is HCl or $H_2SO_4$.

3. The process according to claim 1 wherein the strong base is an alkali metal hydroxide or an alkali metal alkoxide.

4. The process according to claim 3 wherein the base is an alkali metal $C_1$–$C_4$alkoxide.

5. The process according claim 1 wherein the non-polar, essentially water-free solvent is selected from the group consisting of aromatic hydrocarbons, halogenated aromatic hydrocarbons, hydrocarbons, halogenated hydrocarbons, esters and ethers.

6. The process according to claim 5 wherein the solvent is an aromatic hydrocarbon.

7. The process according to claim 6 wherein the solvent is toluene.

8. The process according to claim 7 wherein the base is potassium t-butoxide, sodium methoxide or sodium ethoxide.

9. The process according to claim 8 wherein the base is present at about 1.5 mole to 2.5 mole per mole of formula II diester.

10. The process according to claim 9 for the preparation of a chiral formula I compound selected from the group consisting of (R)2-(4-isopropyl-4-methyl-5-oxo-2-imidazolin-2-yl)nicotinic acid;

(R)2-(4-isopropyl-4-methyl-5-oxo-2-imidazolin-2-yl)-3-quinolincarboxylic acid;

(R)2-(4-isopropyl-4-methyl-5-oxo-2-imidazolin-2-yl)-5-methylnicotinic acid;

(R)5-ethyl-2-(4-isopropyl-4-methyl-5-oxo-2-imidazolin-2-yl)nicotinic acid; and (R)2-(4-isopropyl-4-methyl-5-oxo-2-imidazolin-2-yl)-5-(methoxymethyl)nicotinic acid.

* * * * *